United States Patent
Huang

(10) Patent No.: US 6,238,691 B1
(45) Date of Patent: May 29, 2001

(54) HYDROGEL WOUND DRESSING AND THE METHOD OF MAKING AND USING THE SAME

(75) Inventor: Yeong Hua Huang, St. Louis, MO (US)

(73) Assignee: Sherwood Services AG, Schaffhausen (CH)

( * ) Notice: Subject to any disclaimer, the term of this patent is extended or adjusted under 35 U.S.C. 154(b) by 0 days.

(21) Appl. No.: 08/955,985

(22) Filed: Oct. 22, 1997

Related U.S. Application Data

(60) Provisional application No. 60/029,268, filed on Oct. 24, 1996.

(51) Int. Cl.$^7$ .................................................. A61F 13/00
(52) U.S. Cl. ........................................... 424/443; 424/423
(58) Field of Search ...................................... 424/423, 443

(56) References Cited

U.S. PATENT DOCUMENTS

| | | | |
|---|---|---|---|
| 4,401,651 | * 8/1983 | Knutson | 424/80 |
| 4,960,594 | 10/1990 | Honeycutt | 424/445 |
| 5,106,629 | * 4/1992 | Cartmell et al. | 424/445 |
| 5,118,779 | 6/1992 | Szycher | 528/75 |
| 5,300,291 | 4/1994 | Sablotsky et al. | 424/78.18 |
| 5,357,636 | * 10/1994 | Dresdner, Jr. et al. | 2/161.7 |

\* cited by examiner

Primary Examiner—Jose' G. Dees
Assistant Examiner—Kathryne E. Shelborne
(74) Attorney, Agent, or Firm—Rita D. Vacca; Douglas E. Denninger

(57) ABSTRACT

A hydrogel wound dressing which is highly absorptive, contours to a wound site and maintains the wound in a moist state to promote healing thereof.

21 Claims, No Drawings

HYDROGEL WOUND DRESSING AND THE METHOD OF MAKING AND USING THE SAME

This application claims benefit to U.S. provisional application Ser. No. 60/029,268 filed Oct. 24, 1996.

FIELD OF THE INVENTION

The present invention relates to a hydrogel wound dressing and a method of making and using the same. More particularly, the present invention relates to a flexible hydrogel wound dressing which is highly absorptive, contours to a wound site and maintains the wound in a moist state to promote healing thereof and the method of producing and using the same.

BACKGROUND OF THE INVENTION

The treatment of draining wounds is a problem in the medical profession. Wound exudate such as blood, serum and purulent matter from a draining wound can lead to bacterial growth and delayed healing if not treated properly. Often times it is difficult to maintain wounds free of such wound secretions to allow for healing. Another concern in treating such draining wounds is that some believe that allowing a wound to heal in a slightly moist state may actually accelerate healing. Accordingly, the medical profession desires a means for maintaining draining wounds in a clean, moist protected state.

Currently in an attempt to meet such wound treatment needs there are wound exudate absorption compositions which comprise hydrogel materials in powder form. One example of such a powder material includes dextranomer beads. Dextranomer beads are hydrophilic spherical beads which are applied to a wound to absorb wound exudate. Disadvantages noted in using materials in powder form include difficulty in even application, lumping and clumping of the material after application and difficulty in removal of the material from the wound site without damaging the newly formed tissues of the wound.

U.S. Pat. No. 4,226,232 discloses the blending of a hydrogel material with a liquid curing agent such as polyethylene glycol prior to introducing the material to the wound. A difficulty of using this material is that it can not be sterilized by irradiation due to the formation of free radicals within the gel material. The free radicals within the gel material cause instability of the product and thereby shortens the shelf life thereof.

U.S. Pat. No. 5,059,424 discloses a wound dressing comprising a backing member with an adhesive layer and hydrogel material of 15–30% polyhydric alcohol, 8–14% isophorone diisocyanate prepolymer, 5–10% polyethylene oxide-based diamine, 0–1% salt and the balance water. Difficulties associated with the use of this wound product includes the limitation of not being able to cut the dressing to a size appropriate for the particular wound and still have the backer intact. Additionally, the hydrogel material disclosed in this patent lacks the necessary strength to be used and removed, without the added support of the backer material.

The need exists for a sterile wound dressing that provides a size a appropriate protective covering for a draining wound capable of absorbing exudate from the wound. It is also desirable to have a wound dressing suitable to protect a wound from debris and foreign matter capable of contaminating the wound. It is also desirable to have a wound dressing that cushions the wound from pressure. It is also desirable to have a wound dressing that does not adhere to the new tissue forming in the wound. It is also desirable to have a wound dressing that maintains a wound in a slightly moist state to promote healing.

SUMMARY OF THE INVENTION

The present invention relates to a hydrogel wound dressing capable of absorbing exudate from a draining wound without becoming adhered thereto. The wound dressing maintains the wound in a slightly moist state to promote healing of the wound while retaining its overall strength to allow for removal thereof in a unitary fashion.

The hydrogel wound dressing of the present invention is a polyurethane hydrogel material comprising polyurethane prepolymer, deionized water, glycols and optionally an antimicrobial and/or a bacteriostatic agent.

The method of producing the hydrogel material of the present invention involves hydrolysis and addition reactions to produce a three-dimensional cross-linked polyurethane hydrogel as described in more detail below. The resultant polyurethane hydrogel material is blended and cast molded to allow for gelation thereof in fewer than 180 minutes at room temperature. The subject wound dressing is then optionally subjected to temperatures below 0° C. to remove excess water and then packaged and sterilized using radiation sterilization or other suitable sterilization technique, prior to distribution.

DETAILED DESCRIPTION OF THE INVENTION

The polyurethane hydrogel wound dressing of the present invention is capable of absorbing moisture from a wound site until the overall composition comprises approximately 95 percent to 99 percent water or fluid. The subject non-adhesive hydrogel dressing provides for moist wound healing, absorbs wound exudate, allows for fewer dressing changes, allows for easy removal with no trauma to the wound, protects the wound from contamination and minimizes odor.

The polyurethane hydrogel material of the present invention is generally produced through a hydrolysis and an addition reaction. The hydrolysis and addition reactions are achieved by blending polyurethane prepolymer with polypropylene glycol, water and propylene glycol in accordance with the following reactions:

---

STEP 1:

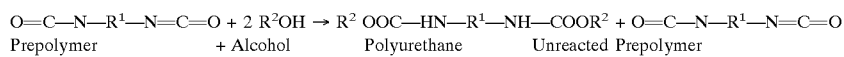

Prepolymer    + Alcohol    Polyurethane    Unreacted Prepolymer

STEP 2:

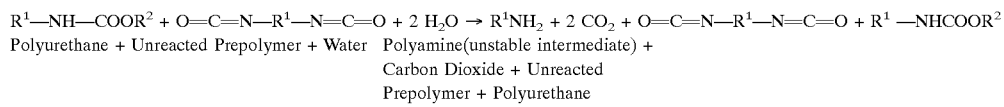

Polyurethane + Unreacted Prepolymer + Water    Polyamine(unstable intermediate) +
Carbon Dioxide + Unreacted
Prepolymer + Polyurethane

STEP 3:

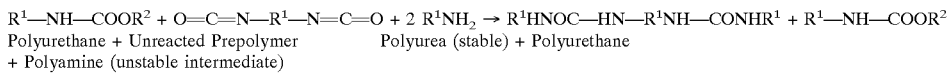

R¹—NH—COOR² + O=C=N—R¹—N=C=O + 2 R¹NH₂ → R¹HNOC—HN—R¹NH—CONHR¹ + R¹—NH—COOR²
Polyurethane + Unreacted Prepolymer           Polyurea (stable) + Polyurethane
+ Polyamine (unstable intermediate)

wherein the $R^1$ groups may be the same or different selected from the group consisting of $C_{1-12}$ alkyl repeating groups such as for example methyl, ethyl, or propyl, but preferably propyl to increase clarity; $C_{1-12}$ mono or poly hydroxyalkyl repeating groups, such as for example hydroxymethyl or dihydroxypropyl but preferably dihydroxypropyl, to increase clarity; $C_{1-12}$ acyl repeating groups, such as for example, acetyl or proprionyl, but preferably proprionyl to increase clarity; $C_{1-12}$ alkoxyalkyl repeating groups, such as, for example, methoxyethyl or ethoxypropyl, but preferably ethoxypropyl to increase clarity; $C_{1-12}$ aminoalkyl repeating groups, such as, for example, aminomethyl or aminopropyl, but preferably aminopropyl to increase clarity; $C_{1-12}$ acylaminoalkyl repeating groups, such as, for example, acetylaminomethyl or proprionylaminomethyl but preferably proprionylaminomethyl to increase clarity; $C_{1-12}$ oxyalkyl repeating groups, such as, but not limited to, oxyethylene, oxypropylene or oxybutylene, but preferably oxyethylene and/or oxypropylene to increase clarity, such repeating units having an average molecular weight of about 7,000 to about 30,000 capped with aromatic, aliphatic, or cycloaliphatic isocyanates, diisocyanates, or polyisocyanates, but most preferably diisocyanate- or polyisocyanate-capped repeating units, as described above, having molecular weights of at least 10,000. The use of aliphatic polyisocyanates is preferred in the present invention to achieve a greater degree of handling freedom, since aliphatic isocyanate-capped prepolymers typically require longer periods of time to gel. In addition, aliphatic polyisocyanates will be preferred when the material is intended to be used in medical applications, because of decreased toxicological considerations. By contrast, prepolymers capped with aromatic polyisocyanates will gel in about 30 to 60 seconds as opposed to 20 to 90 minutes as typical for the aliphatic isocyantes. Gelation within 30 to 60 seconds is a disadvantage for use in the present application due to the lack of adequate time for proper blending of the materials and molding thereof. The subject reaction mixture gels in approximately 15 to 180 minutes at room temperature but preferably approximately 30 to 90 minutes.

Examples of suitable difunctional and polyfunctional isocyanates include, but are not limited to, isophorone diisocyanate; toluene-2,4-diisocyanate; toluene-2,6-diisocyanate; mixtures of toluene-2–4, and 2,6-diisocyanate; ethylene diisocyanate; ethylidene diisocyanate; propylene-1,2-diisocyanate; cyclohexylene-1,2-diisocyanate; cyclohexylene-1,4-diisocyanate; m-phenylene diisocyanate; 3,3'-diphenyl-4,4'-biphenylene diisocyanate; 4,4'-biphenylene diisocyanate; 4,4'-diphenylmethane diisocyanate; 3,3'-dichloro-4,4'-biphenylene diisocyanate; 1,6-hexamethylene diisocyanate; 1,4-tetramethylene diisocyanate; 1,10-decamethylene diisocyanate; cumene-2,4-diisocyanate; 1,5-naphthalene diisocyanate; methylene dicyclohexyl diisocyanate; 1,4-cyclohexylene diisocyanate; p-tetramethyl xylylene diisocyanate; p-phenylene diisocyanate; 4-methoxy-1,3-phenylene diisocyanate; 4-chloro-1,3-phenylene diisocyanate; 4-bromo-1,3-phenylene diisocyanate; 4-ethoxy-1,3-phenylene diisocyanate; 2,4-dimethylene-1,3-phenylene diisocyanate; 5,6-dimethyl-1,3-phenylene diisocyanate; 2,4-diisocyanatodiphenylether; 4,4'-diisocyanatodiphenylether; benzidine diisocyanate; 4,6-dimethyl-1,3-phenylene diisocyanate; 9,10-anthracene diisocyanate; 4,4'-diisocyanatodibenzyl; 3,3'-dimethyl-4,4'-diisocyanatodiphenylmethane; 2,6-dimethyl-4,4'-diisocyanatodiphenyl; 2,4-diisocyanatostilbene; 3,3'-dimethoxy-4,4'-diisocyanatodiphenyl; 1,4-anthracenediisocyanate; 2,5-fluorenediisocyanate; 1,8-naphthalene diisocyanate; 2,6-diisocyanatobenzfuran; 2,4,6-toluene triisocyanate; p,p',p''-triphenylmethane triisocyanate; trifunctional trimer of isophorone diisocyanate; trifunctional biuret of hexamethylenediisocyanate; trifunctional trimer of hexamethylene diisocyanate and polymeric 4,4'-diphenylmethane diisocyanate, preferably diisophorone diisocyanate or isophorone diisocyanate for a preferred rate or gelation.

$R^2OH$ is selected from the group consisting of $C_{1-12}$ monohydric alcohols, such as ethanol, methanol or propanol, wherein propanol is preferred to increase clarity; $C_{1-12}$ diols, such as glycols and derivatives thereof wherein propylene glycol is preferred to increase clarity, and $C_{1-12}$ polyalkyldiols such as polypropylene glycol, polyethylene glycol or polybutylene glycol wherein polypropylene glycol is preferred to increase clarity. Most preferably, propylene glycol and/or polypropylene glycol is used to improve clarity or transparency of the final product. Additionally, $R^2$ represents the corresponding $C_{1-12}$ alkyl group $C_{1-12}$ hydroxyalkyl group, or $C_{1-12}$ polyhydroxyalkyl group derived from $R^2OH$. A clear or transparent product allows for undisturbed viewing of the wound for better wound care management.

The above noted chemical reactions illustrate the process by which the subject hydrogel is produced. In the initial step, as illustrated in STEP 1, a polyurethane prepolymer such as a isophorone diisocyate prepolymer but preferably a prepolymer of the following chemical composition

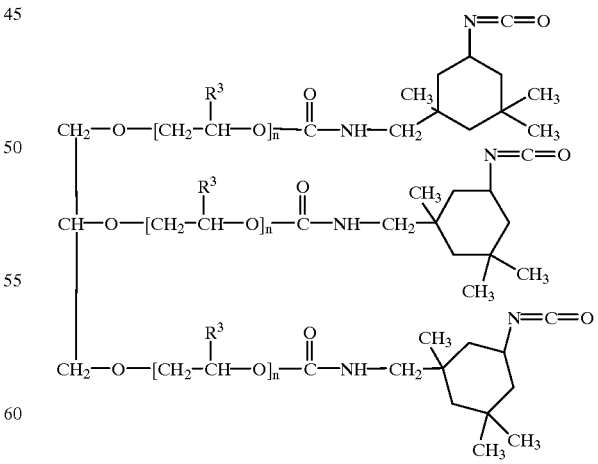

wherein the $R^3$ groups may be the same or different selected from the group consisting of hydrogen, and $C_{1-10}$ alkyl such as for example methyl or ethyl but preferably methyl; and n represents integers which may differ from one another within the range of 1 to 200. A mixture of hydrogen and methyl groups are the preferred $R^3$ groups for the above-described prepolymer in order to increase the flexibility and hydrophilicity of the final product. The prepolymer is reacted with a $C_{1-12}$ alcohol, $C_{1-12}$ diol, $C_{1-12}$ alkyldiol and/or $C_{1-12}$ polyalkyldiol as described above, such as polypropylene glycol or propylene glycol in an alcoholysis reaction to form a polyurethane. Next, as illustrated in STEP 2 unreacted prepolymer further reacts with water to undergo a hydrolysis reaction to form a polyamine and carbon dioxide. Due to the fact that the polyamine produced in STEP 2 is an unstable intermediate in this reaction process, STEP 3 illustrates the continued reaction of the polyamine of STEP 2, undergoing an addition reaction to form a stable polyurea. This series of reactions rather than producing a foam, results in a three-dimensional cross-linked polyurethane/polyurea hydrogel. It is important to note that the water is added at the end of the second step of the procedure in order to prevent premature gelling and foaming. Additionally, the percentage free of isocyanate present in the prepolymer directly affects the gelation reaction rate. For this reason, in the present invention the percentage of free isocyanate present in the reaction mixture is strictly controlled to a level below 5 percent to slow the reaction. Another consideration to be noted is that the faster the reaction rate, the faster the carbon dioxide gas is produced, which if not properly controlled causes the formation of a foam rather than a hydrogel. It is the control of these critical factors, i.e., the percentage of isocyanate present and the reaction rate, among the other considerations noted herein, which allows one to produce the unexpectedly superior hydrogel of the present invention.

In order for one to achieve the desired reaction mixture of the present invention and form a hydrogel of desirable strength and integrity for the intended use, STEP 1 involves blending together approximately 25 to 70 percent of the polyurethane prepolymer but preferably approximately 34.9 percent and approximately 30 to 75 percent of a polyalkyl diol such as polypropylene glycol but preferably approximately 65.1 percent to produce Product A. STEP 2 involves combining approximately 50 to 90 percent deionized water but most preferably approximately 76 percent, approximately 5–15 percent of an alkyl diol such as propylene glycol but preferably about 9.5 percent, and approximately 0 to 40 percent of a polyalkyl diol such as polypropylene glycol but preferably about 14.5 percent to produce Product B to react with Product A. Approximately 15 to 60 percent of Product A but preferably about 43.7 percent is blended with approximately 40 to 85 percent of Product B but preferably about 56.3 percent to produce the desired hydrogel wound dressing of the present invention. Optionally, 0–5% but preferably 1–3% of a antimicrobial or a bacteriostatic agent can be added to the final reaction mixture or Product B. Suitable such antimicrobial and bacteriostatic agents include bismuth tribromophenate, bacitracin, erythromycin, silver sulfadiazine, idoxuridine, triflurouddine, vidarabine, pyrimethamine. Preferably bismuth tribromophenate or silver sulfadiazine are optionally added to the reaction mixture to decrease the risk of infection and odor. The resultant hydrogel wound dressing is characterized in that it comprises 5 to 20 percent by weight of a polyurethane prepolymer, 3 to 45 percent by weight of polypropylene glycols an propylene glycols and the balance water and optional additives.

The polyurethane hydrogel of the present invention is manufactured as further described in the following examples:

EXAMPLE A: HYDROGEN PRODUCED FROM ISOPHORONE DIISOCYANATE BASED PREPOLYMER

Three grams of isophorone diisocyanate prepolymer was mixed thoroughly first with 5.6 grams of polypropylene glycol (Portion A). Then 8.4 grams of deionized water was mixed with 1.05 grams of propylene glycol and 1.6 grams of polypropylene glycol (Portion B). Portion A and Portion B were mixed thoroughly with a stirring rod for about two to 5 minutes until a homogeneous solution was formed. The solution was then cast into a 4"×4" mold and maintained undisturbed for 90 minutes at room temperature while the gelling reaction occurred. The mold was kept in a closed container at room temperature overnight to prevent water evaporation and to permit essentially complete chemical reaction of all isocyanate end groups. The final hydrogel upon removal from the mold was flexible, transparent and able to absorb water four times, i.e., 400 percent, its own weight.

EXAMPLE B: HYDROGEL PRODUCED FROM TOLUENE DIISOCYANATE BASED PREPOLYMER

Five grams of propylene glycol was mixed with five grams of toluene diisocyanate prepolymer (Portion A). Then fifteen grams of deionized water was mixed with seven grams of propylene glycol (Portion B). Portion A and Portion B were quickly mixed and cast into two aluminum weighing dishes. The material gelled within 30 minutes. Both dishes filled with the gelled material were kept in a closed container at room temperature overnight to prevent water evaporation and to permit essentially complete chemical reaction of all isocyanate end groups. The final hydrogel material upon removal from the dishes was flexible, transparent and able to absorb water four times, i.e., 400 percent, its own weight.

EXAMPLE C: HYDROGEL PRODUCED WITH BACTERIOSTATIC AGENT BISMUTH TRIBROMOPHENATE (BTP)

The hydrogel with BTP was formed by repeating the preparation of Example A, except 0.6 grams of BTP was added to Portion B. The final hydrogel was flexible and able to absorb water two and a half times, i.e., 250 percent, its own weight.

EXAMPLE D: HYDROGEN PRODUCED WITH ANTIMICROBIAL SILVER SULFADIAZINE (SSD)

The hydrogel with SSD was formed by repeating the preparation of Example A, except 0.2 grams of SSD was added to Portion B. The final gel was flexible and able to absorb water three times i.e., 300 percent, its weight.

Once the hydrogel is blended as described in detail in the above Examples, the gel may be cast and molded in any size or shape but is preferably molded into ropes having a length ranging from about two to twelve inches but preferably between four to eight inches and a width ranging from 0.1 to 2 inches but preferably about 0.25 to 0.75 inches or into disks having a diameter ranging between one and twelve inches but most preferably between two and six inches for ease of use. The thickness of the disks and ropes may vary substantially from 0.01 to 1 inch in thickness but most preferably are molded to 0.1 inch to 0.5 inch in thickness for ease of use with acceptable absorption.

The unexpected significant advantages of the present hydrogel dressing achieved through the particular reaction ratios noted above include increased absorption capabilities and increased strength. The increased strength of the subject hydrogel material eliminates the need for backing material as described in the prior art. Additionally, the hydrogel is stable, does not become brittle or crack with moisture loss, and has an extended shelf-life over other such materials.

The subject hydrogel dressing so produced is clear unless altered by additives such as bacteriostatic agents and the like. After the hydrogel is cast, molded, and formed, which usually takes approximately one and one half hours at room temperature. The gelling time can be shortened by curing the hydrogel at a higher temperature. The hydrogel once formed may be exposed to low temperatures such as below 0° C. for approximately one half to four hours but preferably approximately one to two hours to extract excess water used to fully complete the reactions as described above. This extraction of excess moisture significantly and unexpectedly increases the absorptive capabilities of the subject wound dressing which is capable of absorbing approximately 2 to 6 times its weight.

The subject hydrogel dressing is packaged and sterilized using an appropriate sterilization technique or may be sterilized and then packaged using aseptic technique. Appropriate methods of sterilization and packaging are known to those skilled in the art and include gamma radiation, electronic beam, ethylene oxide and like methods. Preferably, the subject hydrogel wound dressing is packaged and then sterilized using gamma radiation by cobalt 60 with 1 to 3 mrads but preferably 2 mrads in two independent exposure cycles.

Appropriate packaging for the subject hydrogel wound dressing includes metallic foil pouches such as aluminum foil pouches, polyethylene film, ethylene vinyl acetate film, polypropylene film, polyvinyl chloride film, and like packages known to those skilled in the art but preferably an ethylene vinyl acetate film liner with an aluminum foil pouch as an outer package to maintain moisture level.

The method of using the subject hydrogel wound dressing includes removing the dressing from its packaging and placing the dressing on or in the wound. Depending on the amount of exudate draining from the wound site, the dressing should be changed approximately every 1 to 2 days. The dressing in rope form can also be used for deep tunnel wounds. The dressing may be cut using aseptic technique to a size appropriate for a particular wound before placing the dressing on the wound.

If after cutting the subject wound dressing the unused portion experiences water loss, the same may be rehydrated using aseptic technique and sterilized water.

It is seen therefore that the present hydrogel wound dressing provides an effective moist wound dressing to maintain draining wounds in a clean protected state. The wound dressing and method of making and using the same disclosed herein has specific advantages over the heretofore known means of treating draining wounds. The subject wound dressing eliminates risks associated with the treatment of draining wounds, lessens tissue damage upon removal thereof and may be cut to the appropriate size for ease of placement and use. Hence, for these reasons as well as others, some of which hereinabove set forth, it is seen that the present hydrogel wound dressing represents a significant advancement in the art which has substantial commercial significance.

While there is shown and described herein certain specific embodiments of the invention, it will be manifest to those skilled in the art that various modifications may be made without departing from the spirit and scope of the underlying inventive concept and that the same is not limited to the particular forms herein shown and described except insofar as indicated by the scope of the appended claims.

What is claimed is:

1. A method of producing a hydrogel wound dressing comprising:

forming a first solution of polyurethane prepolymer and polypropylene glycol;

forming a second solution of water, propylene glycol and polypropylene glycol; and combining said first solution with said second solution, to form a reaction mixture, including controlling the amount of free isocyanate present in the reaction mixture to a level below five percent.

2. The method of claim 1 wherein 15 to 60 percent of said first solution is combined with 40 to 85 percent of said second solution.

3. The method of claim 1 wherein 43.7% of said first solution is combined with 56.3% of said second solution.

4. The method of claim 1 wherein said second solution includes a bacteriostatic agent.

5. The method of claim 1 wherein said second solution includes a bacteriostatic agent selected from the group consisting of bismuth tribromophenate, bacitracin and erythromycin.

6. The method of claim 1 wherein said second solution includes bismuth tribromophenate.

7. The method of claim 1 wherein said second solution includes approximately 5 percent by weight bismuth tribromophenate.

8. The method of claim 1 wherein said second solution includes an antimicrobial agent.

9. The method of claim 1 wherein said second solution includes a bacteriostatic agent selected from the group consisting of silver sulfadiazine, idoxuridine, triflurouddine, vidarabine and pyrimethamine.

10. The method of claim 1 wherein said second solution includes silver sulfadiazine.

11. The method of claim 1 wherein said second solution includes approximately 2 percent by weight silver sulfadiazine.

12. A method of using the hydrogel wound dressing produced in claim 1 comprising sterilizing said hydrogel dressing and placing said hydrogel dressing on or in a wound.

13. The method of claim 1 wherein said combined first and second solutions are cast and molded.

14. The method of claim 1 wherein said combined first and second solutions are cast and molded to form a dressing approximately 0.01 inch 1.0 inch thick.

15. The method of claim 1 wherein said combined first and second solutions are cast and molded to form a dressing in the shape of a disc with a diameter ranging from approximately 1.0 inches to 12.0 inches.

16. The method of claim 1 wherein said combined first and second solutions are cast and molded in the shape of a rope with approximately 2 to 12 inches in length and 0.1 to 2.0 inches in width.

17. The method of claim 1 wherein said combined first and second solutions gel in approximately 30 minutes to 120 minutes at room temperature.

18. The method of claim 1 wherein said combined first and second solutions after gelled are exposed to a low temperature for approximately one half to four hours.

19. The method of claim 1 wherein said combined first and second solutions after gelled are exposed to a low temperature of approximately 0° C. for approximately one half to four hours.

20. The method of claim 1 wherein said combined first and second solutions gel to form a hydrogel which may be sterilized.

21. The method of claim 1 wherein said combined first and second solutions gel to form a hydrogel which is sterilized by gamma radiation.

* * * * *